(12) United States Patent
Kim et al.

(10) Patent No.: US 11,980,527 B2
(45) Date of Patent: May 14, 2024

(54) SENSORY SUBSTITUTION APPARATUS AND METHOD

(71) Applicant: Electronics and Telecommunications Research Institute, Daejeon (KR)

(72) Inventors: Moo Seop Kim, Sejong-si (KR); Kyeong Deok Moon, Daejeon (KR); Yun Kyung Park, Daejeon (KR); Chi Yoon Jeong, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 876 days.

(21) Appl. No.: 17/071,611

(22) Filed: Oct. 15, 2020

(65) Prior Publication Data
US 2021/0121656 A1  Apr. 29, 2021

(30) Foreign Application Priority Data

Oct. 24, 2019  (KR) .......... 10-2019-0132848
Sep. 8, 2020  (KR) .......... 10-2020-0114967

(51) Int. Cl.
*A61F 11/04* (2006.01)
*A61F 9/08* (2006.01)
(Continued)

(52) U.S. Cl.
CPC .......... *A61F 11/04* (2013.01); *G16H 20/30* (2018.01); *A61F 9/08* (2013.01); *A61M 21/00* (2013.01);
(Continued)

(58) Field of Classification Search
CPC .......... A61F 11/04; A61F 9/08; G16H 20/30; G16H 20/70; A61M 21/00;
(Continued)

(56) References Cited

U.S. PATENT DOCUMENTS 8,797,386 B2   8/2014  Chou et al.
10,121,335 B2  11/2018  Deokar et al.
(Continued)

FOREIGN PATENT DOCUMENTS

KR   10-1841625   5/2018

*Primary Examiner* — Jeffrey S Vanderveen
(74) *Attorney, Agent, or Firm* — KILE PARK REED & HOUTTEMAN PLLC

(57) ABSTRACT

Provided is a sensory substitution apparatus and method that combines two or more pieces of multi-sense sensory information to be converted into different multi-sense sensory information, in which received pieces of multiple information are combined to suit sensory characteristics of the user's body and efficiently transmitted to a different sensory organ. According to the present invention includes: receiving input sensory information; classifying the input sensory information; calculating an importance of each of individual sensory information; determining a target sense for which part or all of the individual sensory information, of which an importance is calculated, is to be converted into a new sensory signal incongruent with the corresponding individual sense; and converting the input sensory information into target sensory information to be transmitted to the determined target sense which is an organ.

16 Claims, 4 Drawing Sheets

(51) Int. Cl.
*A61M 21/00* (2006.01)
*G16H 20/30* (2018.01)

(52) U.S. Cl.
CPC ............... *A61M 2021/0016* (2013.01); *A61M 2021/0022* (2013.01); *A61M 2021/0027* (2013.01); *A61M 2021/0044* (2013.01)

(58) Field of Classification Search
CPC .. A61M 2021/0016; A61M 2021/0022; A61M 2021/0027; A61M 2021/0044; A61M 2021/005; A61M 2021/0066
See application file for complete search history.

(56) References Cited

U.S. PATENT DOCUMENTS

| | | |
|---|---|---|
| 10,334,202 B1 | 6/2019 | Zhou et al. |
| 2006/0010920 A1 | 1/2006 | Cheo et al. |
| 2017/0343521 A1 | 11/2017 | Chang et al. |

SENSORY SUBSTITUTION APPARATUS AND METHOD

CROSS-REFERENCE TO RELATED APPLICATION

This application claims priority to and the benefit of Korean Patent Applications No. 10-2019-0132848 filed on Oct. 24, 2019 and No. 10-2020-0114967 filed on Sep. 8, 2020, the disclosures of which are incorporated herein by reference in its entirety.

BACKGROUND

1. Field of the Invention

The present invention relates to a technology for converting sensory information into other sensory information, and more specifically, to a technology for combining two or more pieces of sensory information and converting the two or more pieces of sensory information into two or more other sensory signals.

2. Discussion of Related Art

With an increase in elderly or disabled people who have impaired or degraded senses, such as sight and hearing, sensory substitution is gaining great attention as a technical alternative that can improve the impaired sense and perception abilities to ensure continuous economic activity and better quality of life.

In general, sensory substitution refers to changing the form of an impaired or degraded sense into another form of sense and transmitting the changed form of sense into a sensory organ corresponding thereto. Such a sensory substitution technology is known to be based on brain plasticity, in which a human brain is structurally and functionally changed and reorganized to adapt to a new environment. When a sensory ability is lowered or lost, the areas responsible for different pieces of sensory information in the brain's cortex are rearranged. With such a development due to the rearrangement, when a certain sensory organ in the human body loses the function thereof, the organ is functionally replaced with another sensory organ and adapts to the loss.

Existing sensory substitution technologies are restricted to converting a certain single sensory signal of human senses into another sensory signal and transmitting the converted sensory signal. In addition, in some technologies, a plurality of sensory organs are used as transmission paths to transmit a single sensory signal.

However, sensory organs, which are sensory receptors, have different limits of an amount (bandwidth) to which sensory information can be received, and users have different degrees of stimulus of sensory organs to which the users prefer or respond. Accordingly, the existing sensory substitution technologies have a difficulty in effectively transmitting information.

SUMMARY OF THE INVENTION

The present invention provides a sensory substitution technology capable of converting multi-sense sensory information into different sensory information and effectively transmitting the different sensory information to a sensory organ corresponding to the different sensory information.

The technical objectives of the present invention are not limited to the above, and other objectives may become apparent to those of ordinary skill in the art on the basis of the following description.

According to an aspect of the present invention, there is provided a sensory substitution apparatus and method that combines two or more pieces of multi-sense sensory information to be converted into different multi-sense sensory information, in which received pieces of multi-sense sensory information are combined to suit sensory characteristics of the user's body and efficiently transmitted to a different sensory organ. Here, the term "sensory information" refers to specific information used to combine input pieces of sensory information to generate a new form of information (e.g., the position, distance, color, etc. of an object in the case of vision, and analogous specific information in the case of the other senses). In addition, the term "sensory signal" used in the specification represents sensory information in an aspect of a simple signal that receives external information.

Specifically, a sensory substitution apparatus according to an aspect of the present invention includes a sensory information inputter configured to receive a plurality of pieces of different sensory information (multi-sense sensory information), a sensory information combiner configured to combine the received pieces of sensory information to generate a new form of signal and convert the new form of signal into different multi-sense sensory information, and a sensory information outputter configured to output the other sensory information to be transmitted to a sensory organ corresponding to the different sensory information.

Here, the sensory information combiner includes an individual sensory classifier configured to receive multi-sense sensory information having two or more among visual information, auditory information, tactile information, olfactory information, and taste information as piece of input sensory information and classify the input multi-sense sensory information according to individual senses, an importance calculator configured to calculate an importance of the classified individual sensory information, and a sensory information converter configured to determine a target sense for which part of all of the individual sensory information, of which an importance is calculated, is to be converted into a new sensory signal incongruent with the corresponding individual sense, and to convert the input sensory information into target sensory information to be transmitted to the determined target sense.

In addition, a sensory substitution method according to another aspect of the present invention includes: receiving two or more among auditory information, tactile information, olfactory information, and taste information as piece of input sensory information; classifying the piece of input sensory information according to individual senses for efficient combination; calculating an importance of each of pieces of individual sensory information with respect to the classified individual senses; and determining a target sense for which part or all of the individual sensory information, of which an importance is calculated, is to be converted into a new sensory signal incongruent with the corresponding individual sense using the calculated importance or necessary bandwidth information about bandwidths of sensory organs possessed by a user; and converting the input sensory information into target sensory information to be transmitted to the determined target sense (the organ).

Here, the method may optionally further include, in order to determine the above-described necessary bandwidth information, adjusting a bandwidth of the target sense according to the importance calculated for each individual sense.

The constitution and effects of the present invention will become readily apparent with reference to descriptions of the following detailed embodiments when considered in conjunction with the accompanying drawings.

BRIEF DESCRIPTION OF THE DRAWINGS

FIGS. 3A to 3F show examples of intermediate data related to actions of the sensory substitution apparatus and method according to the present invention.

DETAILED DESCRIPTION OF EXEMPLARY EMBODIMENTS

Figure 1:
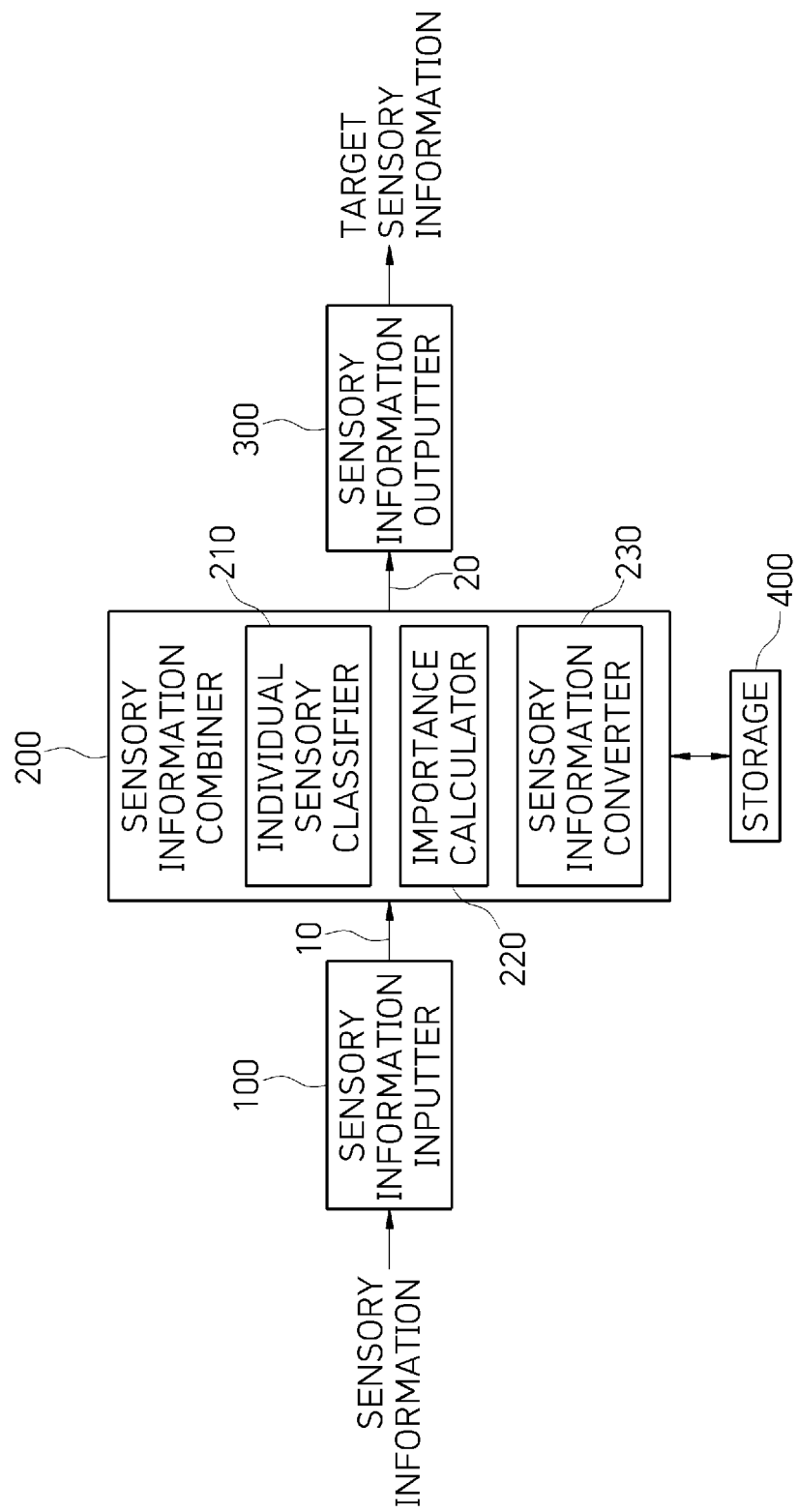
FIG. 1 is a block diagram illustrating an embodiment for implementing a sensory substitution apparatus proposed by the present invention.

Hereinafter, advantages and features of the present invention and manners of achieving them will become readily apparent with reference to descriptions of the following detailed embodiments when considered in conjunction with the accompanying drawings. However, the scope of the present invention is not limited to such embodiments, and the present invention may be embodied in various forms. The embodiments to be described below are embodiments provided only to complete the disclosure of the present invention and assist those skilled in the art in fully understanding the scope of the present invention. The present invention is defined only by the scope of the appended claims. Meanwhile, terms used herein are used to aid in the explanation and understanding of the present invention and are not intended to limit the scope and spirit of the present invention. It should be understood that the singular forms "a," "an," and "the" also include the plural forms unless the context clearly dictates otherwise. The terms "comprises," "comprising," "includes," and/or "including," when used herein, specify the presence of stated features, integers, steps, operations, elements, components and/or groups thereof and do not preclude the presence or addition of one or more other features, integers, steps, operations, elements, components, and/or groups thereof.

Hereinafter, exemplary embodiments of the present invention will be described in detail with reference to the accompanying drawings. In connection with assigning reference numerals to elements in the drawings, the same reference numerals are used to designate the same elements through the whole specification, and in the description of the embodiments, a detailed description of related known functions or constructions will be omitted to avoid obscuring the subject matter of the present invention.

FIG. 1 is a block diagram illustrating an embodiment for implementing a sensory substitution apparatus proposed by the present invention.

The sensory substitution apparatus according to the embodiment includes: a sensory information inputter 100 configured to collect various pieces of sensory information including visual information, auditory information, tactile information, olfactory information, and taste information; a sensory information combiner 200 configured to combine the collected pieces of sensory information (input sensory information) 10 into a new form of sensory signal to generate target sensory information 20; and a sensory information outputter 300 configured to output the converted target sensory information 20 to be transmitted to another sensory organ. In addition, the sensory substitution apparatus may further include a storage 400 configured to store data that is used when the sensory information combiner 200 combines the input pieces of multi-sense sensory information 10 and converts the combined result into the target sensory information 20.

Figure 2:
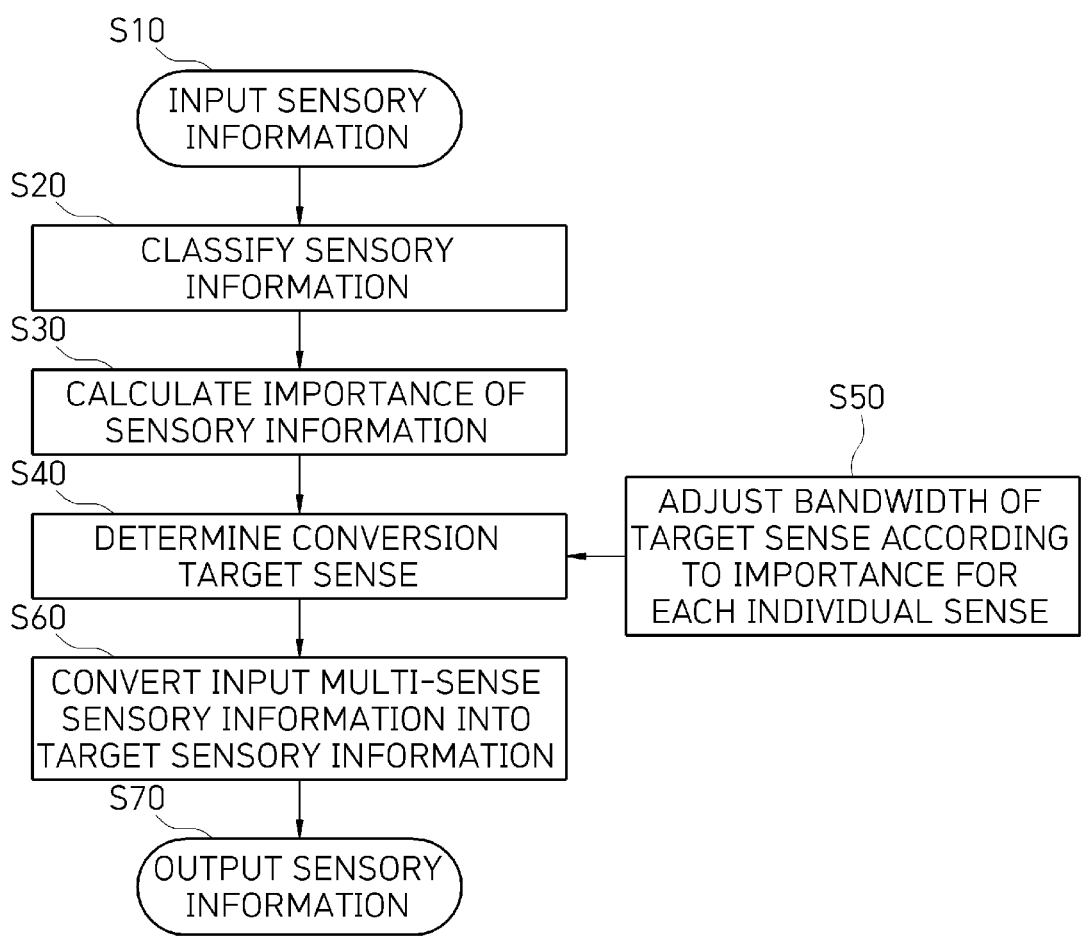
FIG. 2 is a flowchart showing a processing process of a sensory substitution method according to the present invention.

FIG. 2 is a flowchart showing a processing process of a sensory substitution method according to the present invention in which input multi-sense sensory information is combined to convert and generate target sensory information and the converted multi-sense sensory information is output. The process shown in FIG. 2 may be performed by the sensory substitution apparatus shown in FIG. 1 but may also be performed by an apparatus having a configuration different from that shown in FIG. 1. First, to aid in the understanding of the present invention, the overall processing process of the sensory substitution method according to the present invention will be described first with reference to the flowchart of FIG. 2.

Operation S10: Two or more among visual information, auditory information, tactile information, olfactory information, and taste information are input as input sensory information.

Operation S20: The piece of input sensory information are classified by individual senses for efficient combination. In other words, operation S20 is a process of analyzing what types of individual information form pieces of sensory information collected around a user and synchronizing the analyzed pieces of individual sensory information by the occurrence time such that the piece of input sensory information are classified.

Operation S30: The importance of each piece of individual sensory information for the classified individual sense is calculated. In this case, the priority and weight may be used as will be described below.

Operation S40: A target sense for which part or all of the individual sensory information, of which an importance is calculated, is to be converted into a new sensory signal incongruent with the corresponding individual sense is determined. In this case, the importance calculated in operation S30 is used, but the target sense may be determined on the basis of necessary bandwidth information about bandwidths of sensory organs possessed by the user.

Operation S50: As an option, in order to determine the "necessary bandwidth information" described in operation S40, the bandwidth of the target sense may be adjusted according to the importance of each individual sense.

Operation S60: Finally, the input multi-sense sensory information is converted into target sensory information to be transmitted to the determined target sense (a sensory organ).

Operation S70: The target sensory information generated through conversion is output to be transmitted to the corresponding sensory organ.

Hereinafter, the sensory substitution apparatus according to the embodiment of the present invention will be described in detail with reference to FIGS. 1 and 2.

The sensory information inputter 100 receives two or more among visual information, auditory information, tactile information, olfactory information, and taste information as piece of input sensory information 10 and transmits the piece of input sensory information 10 to the sensory information combiner 200. In addition, the sensory information outputter 300 outputs target sensory information 20 that is a result of the input sensory information 10 being combined by the sensory information combiner 200 to be converted into two or more among visual information, auditory information, tactile information, olfactory information, and taste information as piece of different sensory information. Here, the target sensory information 20 is sensory information partially or entirely different from the input sensory information 10.

The sensory information combiner 200 specifically includes an individual sensory classifier 210 configured to classify the pieces of input sensory information 10 according to individual senses for efficient combination; an importance calculator 220 configured to calculate the importance of each individual sense according to a priority and weight (to be described below in detail) with respect to the classified individual senses; and a sensory information converter 230 configured to convert part or all of the individual sensory information, of which an importance is calculated, into sensory information different from the corresponding individual sense.

Various pieces of sensory information perceived by humans each have an importance that is varied according to the situation. In general, humans rely heavily on vision, so visual information is important. However, in a situation where visual dependence is reduced, such as in a dark environment, auditory information or olfactory information is more important than visual information. Therefore, in order to efficiently convert the input sensory information 10 into the target sensory information 20, it is important to identify individual sensory information forming the input multi-sense sensory information 10 in which various pieces of information are mixed.

Therefore, the individual sensory classifier 210 performs a task of analyzing what types of individual information form the pieces of sensory information around the user collected through the sensory information inputter 100 and synchronizing the analyzed pieces of individual sensory information by the occurrence time such that the individual pieces of sensory information are classified. FIG. 3A illustrates an example of grouped data, in which pieces of sensory information input in the form of visual information V, auditory information A, tactile information T, olfactory information S, and taste information E, which need to be transmitted on the basis of each individual sense, are segregated into n items. For example, sensory information for vision may include information, such as a color, a shape, an average luminance of an image, a histogram, and extended information that may be obtained through additional image processing, such as a distance to an object, a location of an object, and a type of an object. Such a segregation of sensory information may be represented by dividing information needing to be transmitted on the basis of each individual sense, such as sight, hearing, touch, smell, taste, etc., into n items, so the value of n indicating the types (the numbers) of pieces of sensory information to be transmitted may vary with each sense.

In addition, the individual sensory classifier 210 may additionally analyze or generate complementary information for the input visual, auditory, tactile, olfactory, and taste information according to the individual sensory information and use the complementary information. In order to generate the additional information according to the individual sensory information, machine learning methods commonly used in data processing may be used. For example, in the case of visual information, in addition to the input image, video, or streaming video, detailed information, such as an object displayed in an image or video, the type of the object, the color of the object, the distance to the object, the distance between the objects, and the location of the object, etc. may be additionally analyzed and used. In addition, when the input sense is a sense of hearing, in addition to sound information, the volume, pitch, tone, and other characteristic values processed in a frequency domain may be generated and used as additional information. When the input information is a sense of touch, information capable of conveying a feeling through the skin, such as pressure, temperature, and intensity of vibration, may be used as the additional information. In the case of smell or taste, information, such as the type, intensity, and duration of smell or taste, may be used as the additional information.

Next, the importance calculator 220 will be described in detail.

The sensory information combiner 200 calculates the importance of each of the pieces of sensory information classified by the individual sense classifier 210 in order to efficiently combine two or more pieces of multi-sense sensory information and combines pieces of current input sensory information 10 using the importance to thereby generate a new form of information. To this end, the importance calculator 220 considers both the importance of pieces of input sensory information 10 and the importance of additional information additionally generated for the individual sense. To aid in the understanding of the present invention, the meanings of the importance, the priority, and the weight will be described below.

[Importance]: The importance in the present invention is an index used to determine a sensory organ that is a target object to which a combination result is finally transmitted, and the importance is calculated for each individual sense (sight: V, hearing: A, touch: T, smell: S, taste: E). In the present invention, weights considered to calculate the importance include a weight D for a change of the input individual sense, a weight W for the individual sense considering a priority, and a weight U for the continuity of the input sense information. Therefore, the importance of each piece of individual sensory information may be calculated as follows.

The importance of visual information: $P_v = D_v + W_v + U_v$
The importance of auditory information: $P_a = D_a + W_a + U_a$
The importance of tactile information: $P_t = D_t + W_t + U_t$
The importance of olfactory information: $P_s = D_s + W_s + U_s$
The importance of taste information: $P_e = D_e + W_e + U_e$ D, W, and V may represent sensory information to be transmitted for each sensory information as n items and may be represented as the sum of the priorities of pieces information desired to be transmitted from an individual sense at an arbitrary point in time. (see FIGS. 3B to 3D) Finally, sensory information generated at an arbitrary point in time is information generated by combining pieces of sensory information ranked high in the order of priority when considering the importance of each individual sense.

[Priority]: The priority is an index used to calculate pieces of information that are preferentially combined for generation among n information groups representing individual senses at an arbitrary point in time. For example, even when the same person is located in the same space and taking the same action (sitting on the sofa), information that is desired to be received may be different. That is, even when the user keeps sitting in the same place, the shape of an object outside the window may be important, or the location of a remote controller of a television (TV) in front of the user may serve as important information.

[Weight]: The weight is a value differentially assigned to a change in sense D, a prioritization of an individual sense W, and a continuity of sense U so as to calculate the most important information from among n information groups representing individual senses at an arbitrary point in time. For example, the weights may be assigned into three levels with 1 for high, 0.5 for medium, and 0.2 for low, such that important sensory information is assigned a great weight. In other way, the weights may be assigned into five levels at uniform intervals with 1 for very high, 0.8 for high, 0.6 for medium, 0.4 for low, and 0.2 for very low.

In summary, in order to determine which sensory information is to be combined for generation from among pieces of input sensory information, the priority is first used to distinguish the most important information at a specific time point in a unit time or discrete time. The priority is related to assigning the weight to sensory information. The weight is a differentiated value used to determine the importance of information in the passage of time and is assigned according to the priorities of individual senses. Weights are assigned as separate values in consideration of the change of a sense D and the continuity of a sense U so that the importance of the individual sense is calculated. In conclusion, target sensory information generated at a specific point in time is information generated by combining pieces of sensory information belonging to individual senses having a high importance.

As such, the importance calculator 220 assigns a weight to each piece of sensory information according to the priorities set to the individual senses classified by the individual sense classifier 210 and the priorities set to the pieces of additional information to calculate the importance, and calculates the importance by summing the assigned weights.

An example of setting the priority for the additional information is as follows. When the individual sense is a sense of sight, the additional information may include at least one of a distance to an object in an image, a color of the object, a location of the object, and a shape of the object. When the individual sense is a sense of hearing, the additional information may include at least one of volume, pitch, and tone. When the individual sense is a sense of touch, the additional information may include at least one of pressure and temperature. Similarly, when the individual sense is a sense of smell or a sense of taste, the additional information may include at least one of the type, intensity, and duration of taste or smell. The setting of the priority using additional information generated from individual sensory information may vary depending on the situation. For example, in the case of additional information for a sense of vision, the priorities may be set in the order of distance, color, location, and shape, but depending on specific circumstances, the priorities may be set in the order of shape, distance, location, and color. In the case of a sense of hearing, the priorities may be set in the order of volume, pitch, and tone, but the priority setting may also vary depending on the situation. Additional information regarding the senses of touch, smell, and taste may also be given with priorities in a similar manner as the above according to the situation.

The importance P, which is used to generate a new signal by combining two or more pieces of sensory information, may be calculated in consideration of the action or environment of the user. To this end, the importance calculator 220 assigns the weight having a value that varies between three conditions as follows.

(1) In consideration of the amount of change D between sensory information input before a preset time and sensory information input at a current time, sensory information with a larger amount of change may be assigned with a higher weight.

(2) On the basis of the priority set according to the situation of the user, the input sensory information may be assigned with a different weight W.

(3) In consideration of the continuity U of transmitted information, sensory information may be assigned with a weight on the basis of a weight assigned to previously input past sensory information. That is, the higher the weight assigned to previous sensory information, the higher the weight is assigned to sensory information of a sense corresponding to the previous sensory information.

In the case of condition (1) above, when the amount of change of current input sensory information is greater than that of a previous signal (previous sensory information), the current input sensory is determined as important information (see FIG. 3B). FIG. 3B is a diagram illustrating representation of data, in which pieces of detailed information to be transmitted on the basis of each individual sense are divided into n groups, for determining a weight D for the amount of change in detailed information about an individual sense at an arbitrary point in time. For example, the weight $D_v$ for the change amount of visual information represents information obtained by reflecting the weight D for the change in detailed information on vision at an arbitrary point in time on a set of pieces of detailed information $\{v_1, v_2, \ldots, v_n\}$ divided into n items. Here, v denotes all of the visual information including detailed information about vision indicated as color information $v_1$, shape of an object $v_2$, distance information $v_3$, and location of an object $v_4$. Similarly, information needing to be transmitted on the basis of other individual senses, such as hearing (a), tactile (t), smell (s), and taste (e), may also be designated in the same manner as the above.

In the case of condition (2), it is considered that the importance of each sensory information varies depending on the situation or action of the user (see FIG. 3C). FIG. 3C is a diagram illustrating representation of data, in which pieces of detailed information to be transmitted on the basis of each individual sense are divided into n groups, for determining a weight W for the priority of detailed information about an individual sense at an arbitrary point in time. For example, the weight $W_v$ for the priority of visual information represents information obtained by reflecting the weight W for the priority of important detailed information on vision at an arbitrary point in time on a set of pieces of detailed information $\{v_1, v_2, \ldots, v_n\}$ divided into n items.

In the case of condition (3) above, it is considered whether to use sensory information input at a previous point in time on the basis of the continuity of transmitted information (see FIG. 3D). FIG. 3D is a diagram illustrating representation of data, in which pieces of detailed information to be transmitted on the basis of each individual sense are divided into n groups, for determining a weight U for the continuity of detailed information about an individual sense at an arbitrary point in time. For example, the weight $U_v$ for the continuity of visual information represents information obtained by reflecting the weight U for the continuity of visual information at each specific time on a set of pieces of detailed information $\{v_1, v_2, \ldots, v_n\}$ divided into n items.

As such, the importance used to generate a new signal by combining two or more pieces of sensory information may be obtained by combining all three pieces of information (P=D+W+U) or combining at least two pieces of information on the basis of the current situation of the user.

Finally, the sensory information converter 230 will be described in detail. As described above, the sensory information converter 230 determines a target sensory organ(s) for which target sensory information is to be transmitted according to the importance reflecting the current situation of the user and converts sensory information into a signal form suitable for the determined target sensory organ, finally generating the target sensory information. In more detail, the sensory information converter 230 includes a target sense determiner configured to determine a target sense, for which sensory information is to be converted, on the basis of at least one of bandwidth information of a sensory organ(s) possessed by a user, environmental information about an environment of a place where the user is located, and action information related to actions performed by the user, and convert pieces of sensory information determined as such into a signal form.

In order to display the generated target sensory information, there is a need to determine pieces of sensory information to which the total amounts of information (i.e., a bandwidth, $B_{target}$) are respectively transmitted. The determination of the target sensory organ target, is achieved according to the calculated importance of the target sensory information and the bandwidths $B_v$, $B_a$, $B_t$, $B_s$, and $B_e$ of information transmittable by individual sensory organs. Target sensory information with a higher importance is first assigned with a transmittable bandwidth of a sensory organ. Accordingly, the target sense determiner determines target senses, for which pieces of sensory information are to be converted, on the basis of necessary bandwidth information about bandwidths of sensory organs possessed by the user. That is, sensory information to be transmitted is determined by the importance and the transmittable bandwidth and is selected in order of highest importance within an available bandwidth range.

The necessary bandwidth of converted sensory information for each sensory information is shown in FIG. 3E. The target sensory organ, to which the target sensory information generated as a new form by combining pieces of sensory information is to be transmitted, is determined by sequentially setting sensory organs starting from a sense having a highest importance among the above described five senses, and the total number of transmission sensory organs is determined by allocating the total amount of information $B_{target}$ needing to be transmitted such that the total amount of information $B_{target}$ is distributed to match with the amounts of information (bandwidths) $B_v$, $B_a$, $B_t$, $B_s$, and $B_e$ transmittable by individual sensory organs. In this case, the generated information is subdivided into m pieces of information in order to transmit the generated information at a predetermined target time, and the bandwidth of an individual sense may be re represented as the sum of the amounts of information (the bandwidths) transmittable at each subdivided time. FIG. 3E is a diagram illustrating the bandwidths of the individual senses.

In the present specification, "target sense" and "target sensory organ" are used with the same meaning and refer to a transmission path (a channel) determined by the target sensory determiner to transmit information generated by combining input sensory information. In addition, "transmission sensory information" refers to information converted into information for a sensory organ which is a determined transmission path. For example, when a signal generated by combining auditory information and olfactory information is to be transmitted through sight and touch, a visual signal as a transmission sensory signal may be detailed information, such as a figure or color of an image or video, and a tactile signal as a transmission sensory signal may be provided in the form of a vibration pattern or a stimulus transmitted to the skin. In the present specification, the term "transmission sensory signal" is also used along with the term "sensory signal-specific converted information."

In addition, the sensory information converter 230 may additionally include a bandwidth adjuster that adjusts the bandwidth of the target sense according to the importance set for each sense. The above description states, "the target sense determiner determines target senses, for which sensory information is to be converted, on the basis of necessary bandwidth information about bandwidths of sensory organs possessed by the user.", wherein, in order to determine the "necessary bandwidth information," the bandwidth adjuster is required. The bandwidth adjuster converts information to be transmitted on the basis of each individual sense by reflecting an environment variable ($\theta_{1-5}$) for each individual sense such that at least one of environmental information on the environment of the place where the user is located and action information on the actions performed by the user is reflected on conversion of information for the determined target senses. Basically, the bandwidth transmittable for each individual sensory organ (indicated as $B_v$, $B_a$, $B_t$, $B_s$, and $B_e$ in the above) exists, but the sense of interest is varied as the intention of a user changes according to the user's environment or action. In other words, information received by the same sensory organ may be changed depending on the situation. Therefore, in order to determine which sense is more important in a certain situation, the amount of transmission is determined by adjusting the environment variable ($\theta$) for each individual sense.

The transmittable bandwidth $B_{target}$ for determining the transmission sensory information is as follows.

Here, $\theta$ has an influence on the amount of transmission $B_{target} = \{\Theta_1 B^T_v + \Theta_2 B^T_s + \Theta_3 B^T_t + \Theta_4 B^T_s + \Theta_5 B^T_e\}$ of the transmission sensory channel and varies depending on the user's surroundings, user's behavior, individual sensory characteristics, and mutual influence of multiple senses. For example, when ambient sound is loud, the environment variable $\theta_2$ has a value less than 1. During movement, since sight suppresses auditory information, a value of the environment variable $\theta_1$ for vision and a value of the environmental variable $\theta_3$ for touch increase in a manner changing according to the situation.

Returning again to FIG. 1, the sensory information outputter 300 synchronizes signals, which are converted for the target sensory organs determined by the sensory information converter 230 and for corresponding pieces of target sensory information according to the bandwidths of the target sensory organs and transmits the signals in the form of multi-sense sensory information into the individual sensory organ. The transmitted multi-sense sensory information is shown in FIG. 3F.

A function or process of each element of the present invention described above may be implemented in a hardware component including at least one of a digital signal processor (DSP), a processor, a controller, an application-specific IC (ASIC), a programmable logic device (e.g., a field programmable gate array (FPGA)), etc.), other electronic devices, or a combination thereof, or may be implemented in software alone or in combination with the hardware component, wherein the software may be stored in a recording medium.

As is apparent from the above, two or more pieces of multi-sense sensory information are received and converted into a plurality of pieces of different target sensory information to be transmitted to a user. In addition, according to the present invention, various conditions are considered in a process of converting input multi-sense sensory information into target sensory information so that a user can be provided with a customized sensory substitution function having an enhanced efficiency.

Although the present invention has been described with reference to the embodiments, a person of ordinary skill in the art should appreciate that various modifications, equivalents, and other embodiments are possible without departing from the scope and spirit of the present invention. Therefore, the embodiments disclosed above should be construed as being illustrative rather than limiting the present invention. The scope of the present invention is not defined by the above embodiments but by the appended claims of the present invention, and the present invention is to cover all modifications, equivalents, and alternatives falling within the spirit and scope of the present invention.

What is claimed is:

1. A sensory substitution apparatus comprising:
a sensory input device that receives multi-sense sensory information having two or more of pieces of sensory information including visual information, auditory information, tactile in nor nation, olfactory information, and taste information,
at least one processor executing an individual sense classifier that receives, from the sensory input device, the multi-sense sensory information having the two or more of pieces of sensory information including visual information, auditory information, tactile information, olfactory information, and taste information that classifies the multi-sense sensory information according to individual senses;
the at least one processor executing an importance calculator that calculates an importance of each individual sensory information classified according to the individual senses;
the at least one processor executing a sensory information converter that determines a target sense for which part or all of the individual sensory information, of which an importance is calculated, is to be converted into a new sensory signal incongruent with the corresponding individual sense, and that converts the input multi-sense sensory information into target sensory information to be transmitted to the determined target sense,
a sensory output device that outputs the target sensory information for use by a sensory organ corresponding to the target sensory information.

2. The sensory substitution apparatus of claim 1, wherein the sensory information converter uses a transmission bandwidth of a sensory organ possessed by a user when determining the target sense.

3. The sensory substitution apparatus of claim 1, wherein the individual sense classifier segregates the pieces of sensory information input in the form of visual information, auditory information, tactile information, olfactory information, and taste information, which need to be transmitted on the basis of each individual sense, into groups.

4. The sensory substitution apparatus of claim 1, wherein the importance calculator, to calculate the importance, assigns a weight to the sensory information in consideration of a change amount between the sensory information input before a preset time and the sensory information input at a current time.

5. The sensory substitution apparatus of claim 1, wherein the importance calculator, to calculate the importance, to calculate the importance, assigns a weight to the sensory information according to a degree of priority set by a situation of a user.

6. The sensory substitution apparatus of claim 1, wherein the importance calculator, to calculate the importance, assigns a weight to the sensory information according to a weight assigned to previously input past sensory information so that continuity of transmitted information is considered.

7. The sensory substitution apparatus of claim 1, wherein the sensory information converter comprises a target sense determiner that determines the target sense, for which the conversion is to be performed, on the basis of at least one of bandwidth information of sensory organs possessed by a user, environmental information about an environment of a place where the user is located, and behavioral information about actions performed by the user, and that converts the determined target sense into a form of a signal.

8. The sensory substitution apparatus of claim 1, wherein the sensory information converter comprises a bandwidth adjuster to adjust a transmittable bandwidth of the target sense according to the importance set for each individual sense.

9. A sensory substitution method comprising:
receiving, through a sensory input device, two or more among visual information, auditory information, tactile information, olfactory information, and taste information as piece of input sensory information;
classifying, by at least one processor, the piece of input sensory information according to individual senses for efficient combination;
calculating, by the at least one processor, an importance of each of pieces of individual sensory information with respect to the classified individual senses;
determining, by the at least one processor, a target sense for which part or all of the individual sensory information, of which an importance is calculated, is to be converted into a new sensory signal incongruent with the corresponding individual sense;
converting, by the at least one processor, the input sensory information into target sensory information to be transmitted to the determined target sense which is an organ; and
outputting, through a sensory output device, the target sensory information for use by a sensory organ corresponding to the target sensory information.

10. The sensory substitution method of claim 9, wherein in the determining of the target sense, a transmittable bandwidth of a sensory organ possessed by a user is additionally used by the at least one processor.

11. The sensory substitution method of claim 9, wherein in the classifying of the individual senses, the pieces of input sensory information in the form of visual information, auditory information, tactile information, olfactory information, and taste information, which needs to be transmitted on the basis of each individual sense, are segregated, by the at least one brocessor, into groups.

12. The sensory substitution method of claim 9, wherein, to calculate the importance, a weight is assigned, by the at least one processor, to the sensory information in consideration of a change amount between the sensory information input before a preset time and the sensory information input at a current time.

13. The sensory substitution method of claim 9, wherein, to calculate the importance, a weight is assigned, by the at least one processor, to the sensory information according to a degree of priority set by a situation of a user.

14. The sensory substitution method of claim 9, wherein, to calculate the importance, a weight is assigned, by the at least one processor, to the sensory information according to a weight assigned to previously input past sensory information so that continuity of transmitted information is considered.

15. The sensory substitution method of claim 9, wherein the converting into the target sensory information comprises determining, by the at least one processor, the target sense, for which the conversion is to be performed, on the basis of at least one of bandwidth information of sensory organs possessed by a user, environmental information about an environment of a place where the user is located, and behavioral information about actions performed by the user and converting the determined target sense into a form of a signal.

16. The sensory substitution method of claim 9, wherein the converting into the target sensory information includes adjusting, by the at least one processor, a transmittable bandwidth of the target sense according to the importance set for each individual sense.

\* \* \* \* \*